(12) United States Patent
Crowley

(10) Patent No.: US 6,185,443 B1
(45) Date of Patent: Feb. 6, 2001

(54) VISIBLE DISPLAY FOR AN INTERVENTIONAL DEVICE

(75) Inventor: Robert J. Crowley, Sudbury, MA (US)

(73) Assignee: Boston Scientific Corporation, Natick, MA (US)

(*) Notice: Under 35 U.S.C. 154(b), the term of this patent shall be extended for 0 days.

(21) Appl. No.: 08/939,612

(22) Filed: Sep. 29, 1997

(51) Int. Cl.[7] ............................................. A61B 5/05
(52) U.S. Cl. .................. 600/407; 600/476; 600/473; 600/478
(58) Field of Search .................. 600/407, 424, 600/411, 414, 426, 476, 427, 478, 549, 436, 437, 438, 473; 606/130; 374/100, 170, 180, 187, 191

(56) References Cited

U.S. PATENT DOCUMENTS

| | | | |
|---|---|---|---|
| 2,002,559 | 5/1935 | Wappler | 174/39 |
| 2,583,937 | 1/1952 | Fossati | 128/4 |
| 3,176,114 | 3/1965 | Kneisley | 219/223 |
| 4,233,493 | 11/1980 | Nath | 219/354 |
| 4,274,706 | 6/1981 | Tangonan | 350/96.19 |
| 4,289,966 | 9/1981 | Roberts | 250/378 |
| 4,340,307 | 7/1982 | Diamond et al. | 356/418 |
| 4,472,728 | 9/1984 | Grant et al. | 357/30 |
| 4,541,272 | 9/1985 | Bause | 73/118 |
| 4,548,505 | 10/1985 | Ono | 356/445 |
| 4,556,057 | 12/1985 | Hiruma et al. . | |
| 4,560,286 * | 12/1985 | Wickersheim | 600/549 |
| 4,570,638 | 2/1986 | Stoddart et al. . | |
| 4,578,061 | 3/1986 | Lemelson . | |
| 4,672,972 | 6/1987 | Berke | 128/653 |
| 4,718,417 | 1/1988 | Kittrell et al. | 128/303.1 |
| 4,803,992 | 2/1989 | Lemelson . | |
| 4,813,790 * | 3/1989 | Frankel et al. | 600/549 |
| 4,872,458 | 10/1989 | Kanshira et al. | 128/401 |
| 4,882,623 | 11/1989 | Uchikubo | 358/98 |
| 4,894,547 | 1/1990 | Leffell et al. . | |
| 4,895,156 * | 1/1990 | Schulze | 600/310 |
| 4,898,175 * | 2/1990 | Noguchi | 600/310 |
| 4,902,896 | 2/1990 | Fertig, Sr. et al. | 290/348 |
| 4,928,172 | 5/1990 | Uehara et al. | 358/98 |
| 4,930,516 | 6/1990 | Alfano et al. . | |
| 4,938,602 | 7/1990 | May et al. | 356/435 |
| 4,981,138 | 1/1991 | Deckelbaum et al. | 128/665 |
| 5,001,556 | 3/1991 | Nakamura et al. | 358/98 |
| 5,009,655 | 4/1991 | Daignault, Jr. et al. | 606/7 |
| 5,021,888 | 6/1991 | Kondou et al. | 358/213.11 |
| 5,034,010 | 7/1991 | Kittrell et al. . | |
| 5,036,853 | 8/1991 | Jeffcoat et al. . | |
| 5,042,494 | 8/1991 | Alfano | 128/665 |
| 5,045,056 | 9/1991 | Behl | 604/49 |
| 5,056,503 | 10/1991 | Nagasaki et al. | 128/6 |

(List continued on next page.)

FOREIGN PATENT DOCUMENTS

| | | |
|---|---|---|
| 888727 | 7/1949 | (DE) . |
| 30 23 130 | 1/1982 | (DE) . |
| 40 05 743 | 8/1991 | (DE) . |

(List continued on next page.)

OTHER PUBLICATIONS

International Search Report for PCT/US97/20324 dated Mar. 11, 1998.
International Search Report for PCT/US98/20019 dated Jan. 20, 1999.

(List continued on next page.)

Primary Examiner—Brian L. Casler
(74) Attorney, Agent, or Firm—Testa, Hurwitz & Thibeault, LLP

(57) ABSTRACT

A display is located on an interventional device insertible into a body. More specifically, the display is located on a distal end of the device and is coupled to a sensing system. The sensing system senses a bodily condition. The display receives the sensed bodily condition and displays a signal indicative of the bodily condition within a pre-existing field of view.

21 Claims, 5 Drawing Sheets

U.S. PATENT DOCUMENTS

| | | |
|---|---|---|
| 5,062,428 | 11/1991 | Chance . |
| 5,106,387 | 4/1992 | Kittrell et al. .......................... 606/15 |
| 5,115,137 | 5/1992 | Andersson-Engels et al. . |
| 5,116,759 | 5/1992 | Klainer et al. ....................... 435/288 |
| 5,125,404 | 6/1992 | Kittrell et al. . |
| 5,127,407 | 7/1992 | Tan ...................................... 128/633 |
| 5,131,398 | 7/1992 | Alfano et al. ........................ 128/665 |
| 5,166,755 | 11/1992 | Gat ....................................... 356/419 |
| 5,172,693 | 12/1992 | Doody . |
| 5,174,297 | 12/1992 | Daikuzono . |
| 5,187,572 | 2/1993 | Nakamura et al. ..................... 358/98 |
| 5,187,672 | 2/1993 | Chance et al. . |
| 5,193,542 | 3/1993 | Missanelli et al. . |
| 5,197,470 | 3/1993 | Helfer et al. . |
| 5,201,318 | 4/1993 | Rava et al. . |
| 5,206,174 | 4/1993 | Gehrke et al. .......................... 436/58 |
| 5,213,569 | 5/1993 | Davis .................................... 604/22 |
| 5,233,621 | 8/1993 | Lawandy ............................... 372/22 |
| 5,242,437 | 9/1993 | Everett et al. ......................... 606/15 |
| 5,261,410 | 11/1993 | Alfano et al. . |
| 5,262,645 | 11/1993 | Lambert et al. ..................... 250/339 |
| 5,304,173 | 4/1994 | Kittrell et al. ......................... 606/15 |
| 5,305,748 | 4/1994 | Wilk . |
| 5,309,907 | 5/1994 | Fang et al. ........................... 128/633 |
| 5,318,024 | 6/1994 | Kittrell et al. ....................... 128/634 |
| 5,348,018 | 9/1994 | Alfano et al. . |
| 5,350,375 | 9/1994 | Deckelbaum et al. ................... 606/7 |
| 5,351,532 | 10/1994 | Hager .................................... 73/153 |
| 5,377,676 | 1/1995 | Vari et al. ............................ 128/634 |
| 5,383,467 | 1/1995 | Auer et al. . |
| 5,386,827 | 2/1995 | Chance et al. . |
| 5,398,844 | 3/1995 | Zaslavsky et al. ................... 221/208 |
| 5,402,778 | 4/1995 | Chance . |
| 5,402,792 | 4/1995 | Kimura ........................... 128/663.01 |
| 5,402,801 * | 4/1995 | Taylor ................................. 128/898 |
| 5,405,369 | 4/1995 | Selman et al. ........................ 607/88 |
| 5,408,998 * | 4/1995 | Mersch ................................ 600/309 |
| 5,413,108 | 5/1995 | Alfano . |
| 5,417,207 | 5/1995 | Young et al. ........................ 128/634 |
| 5,417,210 * | 5/1995 | Funda et al. ......................... 600/407 |
| 5,419,323 | 5/1995 | Kittrell et al. . |
| 5,421,337 | 6/1995 | Richard-Kortum et al. . |
| 5,421,339 | 6/1995 | Ramanujam et al. . |
| 5,445,608 | 8/1995 | Chen et al. ............................ 604/20 |
| 5,452,723 | 9/1995 | Wu . |
| 5,456,252 | 10/1995 | Vari . |
| 5,461,229 | 10/1995 | Sauter et al. ........................ 250/253 |
| 5,467,767 | 11/1995 | Alfano et al. ........................ 128/665 |
| 5,512,757 | 4/1996 | Cederstand . |
| 5,517,313 | 5/1996 | Colvin, Jr. . |
| 5,517,997 * | 5/1996 | Fontenot ............................. 600/473 |
| 5,540,691 * | 7/1996 | Elstrom et al. ........................ 606/64 |
| 5,542,928 | 8/1996 | Evans et al. ......................... 604/113 |
| 5,545,897 | 8/1996 | Jack . |
| 5,553,614 | 9/1996 | Chance . |
| 5,555,885 | 9/1996 | Chance . |
| 5,556,421 | 9/1996 | Prutchi et al. ......................... 607/36 |
| 5,562,100 | 10/1996 | Kittrell . |
| 5,571,152 | 11/1996 | Chen et al. ............................ 607/92 |
| 5,579,773 | 12/1996 | Vo-Dinh . |
| 5,596,988 * | 1/1997 | Markle et al. ........................ 600/310 |
| 5,626,139 * | 5/1997 | Szeles et al. ......................... 600/473 |
| 5,632,740 | 5/1997 | Koch et al. . |
| 5,647,368 | 7/1997 | Zeng et al. ........................... 126/665 |
| 5,730,134 * | 3/1998 | Dumoulin et al. ................... 600/407 |
| 5,769,791 | 6/1998 | Benaron et al. . |
| 5,785,658 | 7/1998 | Benaron et al. . |
| 5,800,478 * | 9/1998 | Chen et al. ............................ 607/88 |
| 5,807,261 | 9/1998 | Benaron et al. . |
| 5,829,878 * | 11/1998 | Weiss et al. ......................... 600/549 |
| 5,885,293 * | 3/1999 | McDevitt ............................... 606/80 |
| 5,928,137 * | 7/1999 | Green .................................. 600/160 |

FOREIGN PATENT DOCUMENTS

| | | |
|---|---|---|
| 195 12 518 | 10/1995 | (DE) . |
| 0 314 937 | 10/1988 | (EP) . |
| 0 304 321 | 9/1992 | (EP) . |
| 0 629 380 | 12/1994 | (EP) . |
| 0 650 694 A1 | 5/1995 | (EP) . |
| 0 728 440 | 8/1996 | (EP) . |
| 0 777 119 | 6/1997 | (EP) . |
| 0 792 618 | 9/1997 | (EP) . |
| 0 920 831 | 6/1999 | (EP) . |
| 2-223828 | 9/1990 | (JP) . |
| 7-88105 | 4/1995 | (JP) . |
| 7-289506 | 11/1995 | (JP) . |
| 8-83569 | 3/1996 | (JP) . |
| 9-192138 | 7/1997 | (JP) . |
| WO 90/04352 | 5/1990 | (WO) . |
| WO 90/12536 | 11/1990 | (WO) . |
| WO 91/15151 | 10/1991 | (WO) . |
| WO 92/14514 | 9/1992 | (WO) . |
| WO 92/15253 | 9/1992 | (WO) . |
| WO 94/13191 | 6/1994 | (WO) . |
| WO 95/12349 | 5/1995 | (WO) . |
| WO 96/05693 | 2/1996 | (WO) . |
| WO 96/07451 | 3/1996 | (WO) . |
| WO 96/24406 | 8/1996 | (WO) . |
| WO 96/39932 | 12/1996 | (WO) . |
| WO 97/01985 | 1/1997 | (WO) . |
| WO 98/22805 | 5/1998 | (WO) . |

OTHER PUBLICATIONS

International Search Report for PCT/US98/20018 dated Jan. 21, 1999.

International Search Report for PCT/US98/21100 dated Feb. 8, 1999.

Petrofsky, "In Vivo Measurement of Brain Blood Flow in the Cat," *IEEE Transaction on Biomedical Engineering*; vol. BME–26, No. 8: 441–445 (Aug. 1979).

Internet Publication, http://iqe.ethz.ch/~fpst/Final Report/M4/M4P04–1.html.

Kopp et al., "Stay Tuned: Photonic Filters Color Your World," *Photonics Spectra*, Mar. 1997, pp. 125–129.

Coleman et al., "Acoustic Emission and Sonoluminescence Due to Cavitation at the Beam Focus of an Electrohydraulic Shock Wave Lithotripter", *Ultrasound in Med. Biol*, vol. 18, No. 3, pp. 267–281 (1992).

Vona et al., "A Test of the Hypothesis that Cavitation at the Focal Area of an Extracorporeal Shock Wave Lithotripter Produces Far Ultraviolet and Soft X–Ray Emissions", *J. Acoust, Soc. Am.*, vol. 98 (2), pp. 706–711, (Aug. 1995).

Ko, Biomedical Sensors and Actuators, Electronics Engineers' Handbook, McGraw–Hill 1989, pp 26–53 –26–68.

Meindl, J. Implantable Telemetry in Biomedical Research, Electronics Engineers' Handbook, McGraw–Hill 1989, pp 26–41 –25–53.

Cothren et al., "Gastrointestinal Tissue Diagnosis by Laser–Induced Fluorescence Spectroscopy at Endoscopy" *Gasto Endoscopy*, vol. 36 No. 2, pp. 105–111, 1990.

Kapadia et al, "Laser–induced fluorescence spectroscopy of human clonic mucosa", *Gastroentrerology*, vol. 29, pp. 150–157, 1990.

Lilge et al., "Light Induced Fluorescennce Spectroscopy at Endoscopy", *Presented at the 10th Asisan Pacific Congress of Gastroenterology*, 1996.

Huang et al., "Fluoresence Diagnosis of Gynecological Cancerous and Normal Tissues", *SPIE*, vol. 2135, pp. 42–44, 1994.

Anidjar et al., "Ultraviolet Laser–Induced Autofluorescence Distinction Between Malignant and Normal Urothelial Cells and Tissues", *Journal of Biomedical Optics*, vol. 1, No. 3, pp. 335–341, 1996.

Crowley et al., "Ultrasound Guided Therapeutic Catherters: Recent Developments and Clinical Results", *The International Journal of Cardiac Imaging*, vol. 6, pp. 145–156, 1991.

International Search Report for PCT/US97/20367.

International Serach Report for PCT/US97/20435.

* cited by examiner

VISIBLE DISPLAY FOR AN INTERVENTIONAL DEVICE

FIELD OF THE INVENTION

The invention relates generally to interventional devices for use in a body. More particularly, the invention relates to a visible display located at the distal end of an interventional device for use in a body.

BACKGROUND OF THE INVENTION

Interventional devices are used to perform minimally invasive diagnostic and therapeutic procedures. The interventional device can include, without limitation, a catheter, an endoscope, a guide wire, a needle or an introducer. Endoscopes, for example, provide high-resolution detailed views of internal organs and body cavities. Typically, catheters and other interventional devices are used in conjunction with endoscopes to provide an auxiliary diagnostic or therapeutic capability. Positioning and guidance of the interventional device is accomplished readily by direct observation.

Recently, optical biopsy, ultrasound, and other sensor-based diagnostic devices have been incorporated into the interventional device which is used in conjunction with an endoscope and an auxiliary viewing, analysis or externally indicating console. These devices can include an image overlay, numeric data, or other information needed to quantify or recognize a biological (or morphological) region or condition. Attempts have been made to overlay this information onto existing video displays commonly used with endoscopes to provide an image that is easier to interpret and does not require the switching of display screens or otherwise divert the attention of the doctor to other indicia. Adoption of these displays has been slow, however, due to the need to hardwire attachments and other electronics onto existing devices. The adoption process has been further slowed by the need for extensive testing of these attachments to obtain regulatory approvals.

SUMMARY OF THE INVENTION

It is therefore an object of the present invention to display the additionally available information (e.g., an image, data, or graphical display) within the field of view provided by available interventional devices without the need for device modifications. It is another object of the invention to provide a display which can be included within the interventional device. It is yet another object of the invention to provide a display that is easy to use, requires minimal integration into interventional devices, and readily adaptable to a variety of interventional devices. It is yet another object of the invention to provide a display in conjunction with other integrated imaging, sensing or therapeutic devices cost-effectively and with minimum support hardware or capital equipment. It is yet another object of the invention to provide for disposability and modularity which are beneficial for all interventional devices.

The present invention realizes the foregoing objects and provides additional capabilities, benefits and features. In one aspect, the invention features a display located on a distal end of an interventional device. The display includes an indicator for providing a signal indicative of a bodily condition. The indicator provides a visible signal indicative of the bodily condition within a pre-existing field of view of the interventional device or of a remote display system. The indicator can comprise at least one of the following light emitters (a) a light emitting diode, (b) a liquid crystal display, or (c) a projection display. The indicator can also comprises at least one of the following (a) an optical emitter, (b) a chemical indicator, or (c) a polymeric emitter. The chemical indicator can comprise litmus paper, and the polymeric emitter can comprise at least one organic light emitting diode.

In a detailed embodiment, the display can also include a power source and a sensing system located in the distal end of the interventional device. The power source provides power to the display and can be a small battery. The sensing system provides a signal indicative of the sensed bodily condition to the indicator. The sensing system comprises a sensor or a light source in combination with a light detector. The detector is adapted for monitoring light emissions from the light source. A filter can be disposed adjacent the detector for selectively detecting light emissions having a pre-determined wavelength. Multiple batteries, sensors, light sources, light detectors and filters can be used.

In another aspect, the invention features an interventional device comprising an elongated member and a display. The elongated member is insertible into a body for diagnostic and/or therapeutic procedures. A sensing system disposed in the distal end of the elongated member senses a bodily condition. The display is located on a distal end of the elongated member and is coupled to the sensing system for receiving the sensed bodily condition. The display provides a signal indicative of the sensed bodily condition.

The display can include an indicator for providing the signal indicative of the bodily condition within a pre-existing field of view of the interventional device or of a remote display system. The indicator can comprise at least one of the following (a) a light remitter, (b) an optical emitter, (c) a chemical indicator, or (d) a polymeric emitter.

The interventional device can also include a power source and a sensing system located in the distal end of the interventional device. The power source provides power to the display. The sensing system comprises a sensor or a light source in combination with a light detector. A filter disposed adjacent the detector selectively detects light emissions having a pre-determined wavelength. Multiple power sources, sensors, light sources, light detectors and filters can be used.

In yet another aspect, the invention features a method for observing a signal indicative of a bodily condition. An interventional device having a display located on a distal end thereof is inserted into a body. The interventional device contacts tissue in the body to sense a bodily condition therefrom. A signal indicative of the sensed bodily condition can be viewed on the display.

In yet another aspect, the invention features a method for displaying a signal indicative of a bodily condition. An interventional device having a display located on a distal end thereof is inserted into a body. The interventional device is manipulated to contact a region in the body for sensing a bodily condition therefrom. A signal indicative of the sensed bodily condition can be viewed on the display within a pre-existing field of view.

DETAILED DESCRIPTION

Figure 1:
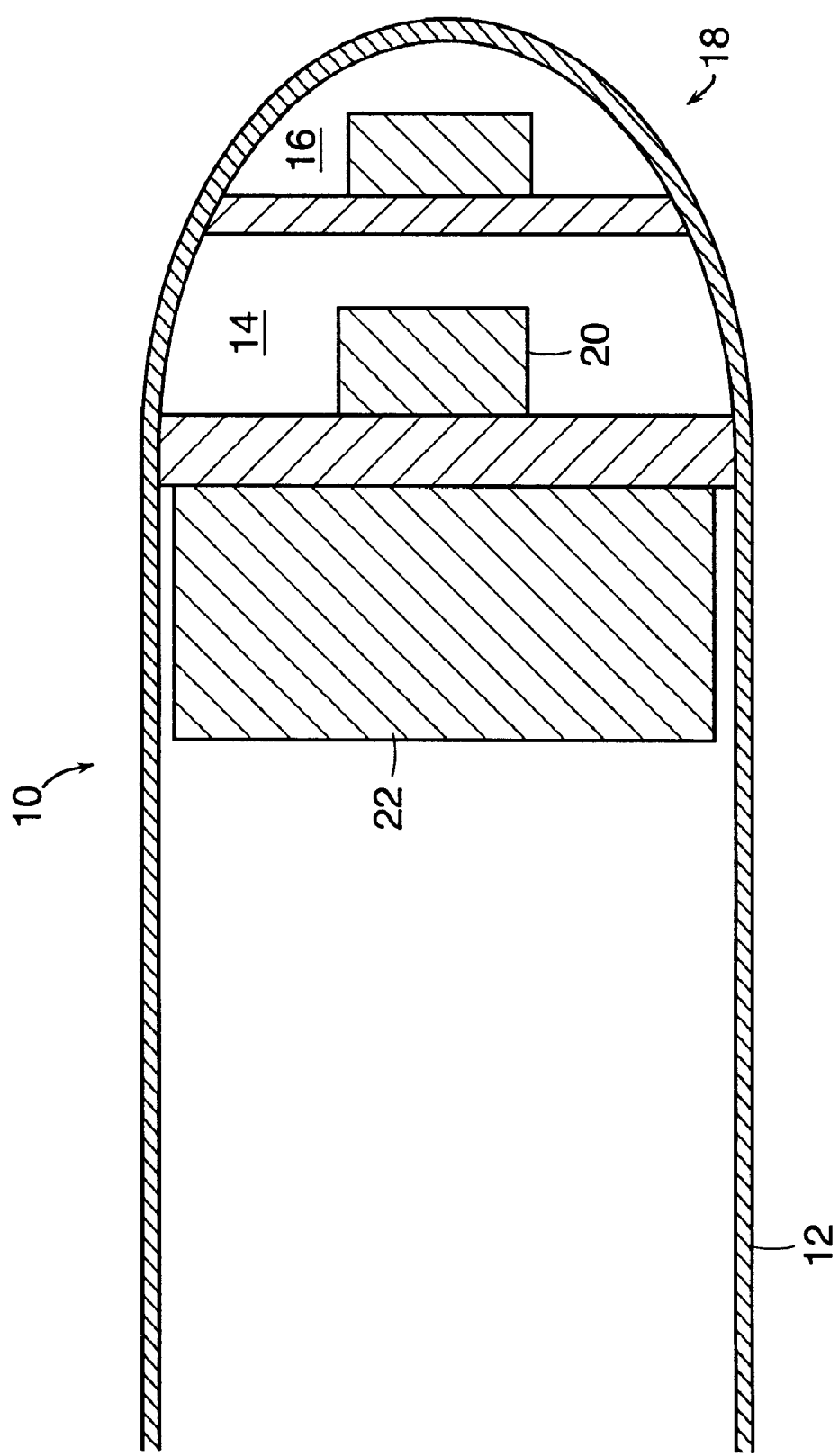
FIG. 1 is a cross-sectional view of an interventional device including a display located at the distal end of the interventional device.

Referring to FIG. 1, an interventional device 10 includes an elongated member 12 and a display 14. The elongated member 12 can be inserted into a body for diagnostic and/or therapeutic procedures. The display 14 is located at the distal end of the elongated member 12. A sensing system 16, which is also located the distal end 18 of the elongated member 12, senses a bodily condition. The display 14 receives the sensed bodily condition from the sensing system 16 and displays a signal indicative of the sensed bodily condition.

More specifically, the display 14 includes an indicator 20 that provides a visible signal indicative of the bodily condition within a pre-existing field of view of the interventional device or of a remote display system. The indicator 20 can comprise at least one of the following: (a) light emitters (e.g., a light emitting diode, a liquid crystal display or a multi-color display); (b) an optical emitter, (b) a chemical indicator (e.g., litmus paper); or (c) a polymeric emitter (e.g., an organic light emitting diode). The indicator 20 can indicate states, such as ON or OFF, a numeral, letter, shape or image. In addition, the indicator 20 be a projection display that projects indicia upon the interventional device or on tissue. A projection display can include a light emitter focused by a lens and scanned with a 2-axis piezoelectric scanner. Other types of projection displays, which are known in the art, can be used.

The interventional device can also include a power source 22 in the distal end of the interventional device. The power source 22 provides power to the display 14 and can be a small battery.

In one embodiment, the sensing system 16 can comprises a sensor or a light source in combination with a light detector. The detector is adapted for monitoring light emissions from the light source. In another embodiment, the sensing system 16 can comprises a sensor which when disposed in close proximity to a changed bodily condition, varies the power source 22 and provide a signal to the display 14. The sensor can be an arrangement of electrodes which allows current to flow from a separate source (e.g., a battery) when the electrodes are placed in a conductive fluid (e.g., saline). The current passed can also power a small light bulb to indicate to the user that the electrodes are in good contact with the tissue under examination. In yet another embodiment, the sensing system 16 can be a fluorescence detection system. Such a system is described in commonly owned U.S. patent application, Ser. No. 08/898,604, entitled, "Miniature Spectrometer" by Robert J. Crowley, which is incorporate herein by reference. In another embodiment, an impedance sensing system, which is used with certain RF ablation techniques, can be employed. In these techniques, tissue to be destroyed by the application of RF energy may be subject to charring or incomplete ablation if certain electrical contact conditions, such as the resistance of an electrode in contact with tissue, exist. Such conditions can be monitored and displayed on the display 14. In yet another embodiment, chemical specific sensors can be used.

Such sensors can be electronically coupled to the display or can be a simple chemical indicator such as litmus paper. The electrical (chemical) sensors may have receptor channels upon which specific molecules are known to preferentially adhere. Sufficient molecules in an area of these sensors may accumulate to cause a change in the electrical resistance of the sensor, and such change can be quickly, efficiently and inexpensively be displayed on the display.

Figure 2:
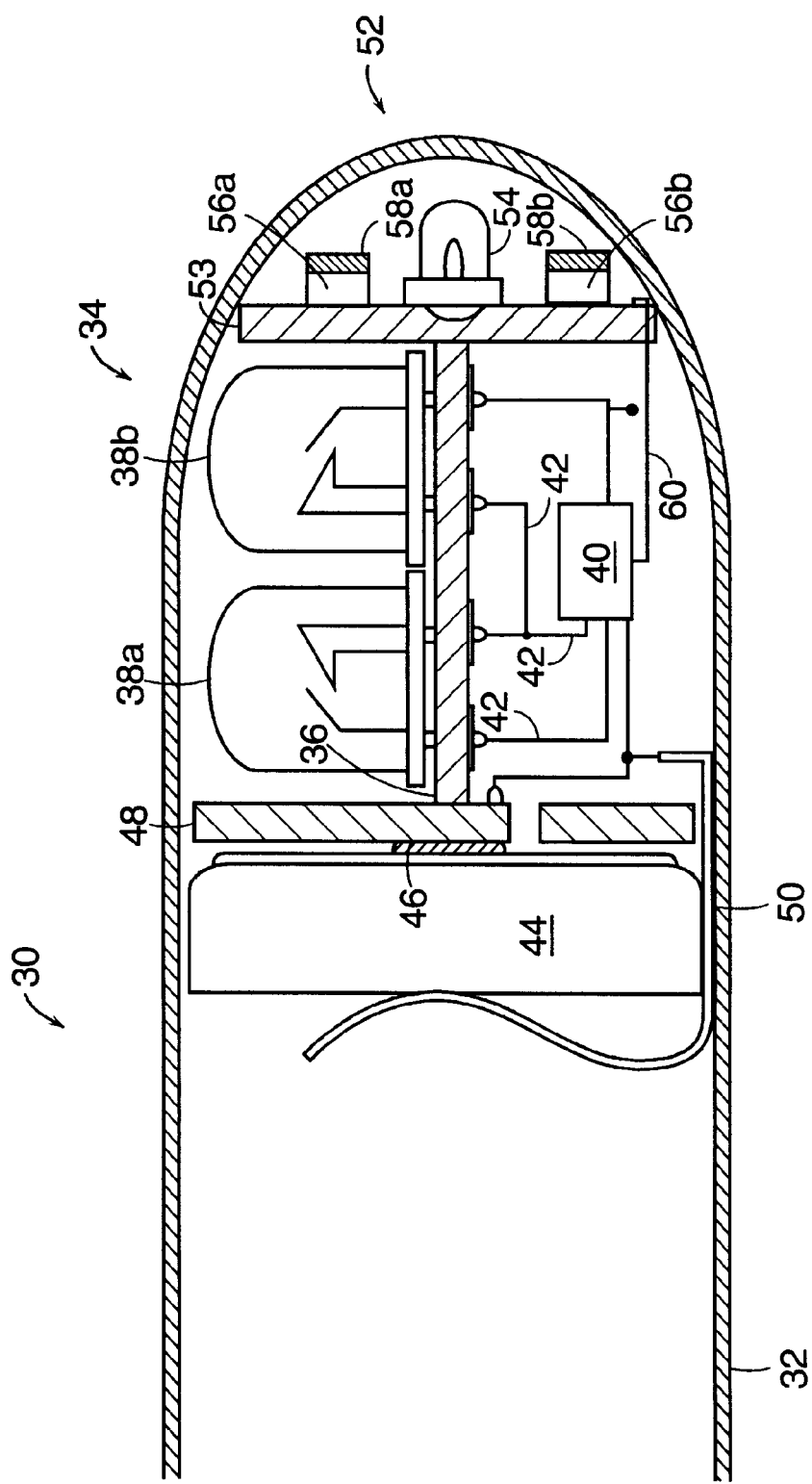
FIG. 2 is a cross-sectional view of an interventional device including a light source, detectors, a display, a signal processor and a power source located at the distal end of the interventional device.

Referring to FIG. 2, an interventional device 30 includes an elongated member 32 insertible into a body (not shown) for diagnostic and/or therapeutic procedures. A display 34 is mounted onto a mounting structure 36 at the distal end of the elongated member 32. The display 34 includes a pair of light emitting diodes (LEDs) 38a, 38b for providing a visible signal indicative of the bodily condition within a pre-existing field of view. The LEDs 38a, 38b are electrically connected to a signal processor 40 via electrical lines 42. A power source 44 provides power to the display via an electrical contact 46, the signal processor 40 and electrical lines 41, 42. The power source 44 is located adjacent a mounting structure 48 and secured by a ground spring 50. The sensing system 52 is mounted to a mounting structure 53 at the distal end of the interventional device 30 and comprises an LED 54 and a pair of detectors 56a, 56b. Filters 58a, 58b can be disposed adjacent the detectors 56a, 56b.

In operation, the LED 54 emits light that impinges upon tissue under examination. The detectors 56a, 56b in combination with the filters 58a, 58b selectively detecting spectral emissions (e.g., fluorescence emitted by the tissue with a pre-determined wavelength range. The detectors 56a, 56b are electrically connected to the processor 40 via the signal line 60. In response to the signals received from the detectors 56a, 56b, the processor 40 provides a signal indicative of a bodily condition to one of the LEDs 38a, 38b. One of the LEDs turns ON to provide an indication of the sensed bodily condition. The distal end of the intervention device is at least semi-transparent, thereby allowing the user to readily observe the activated LED.

Figure 3:
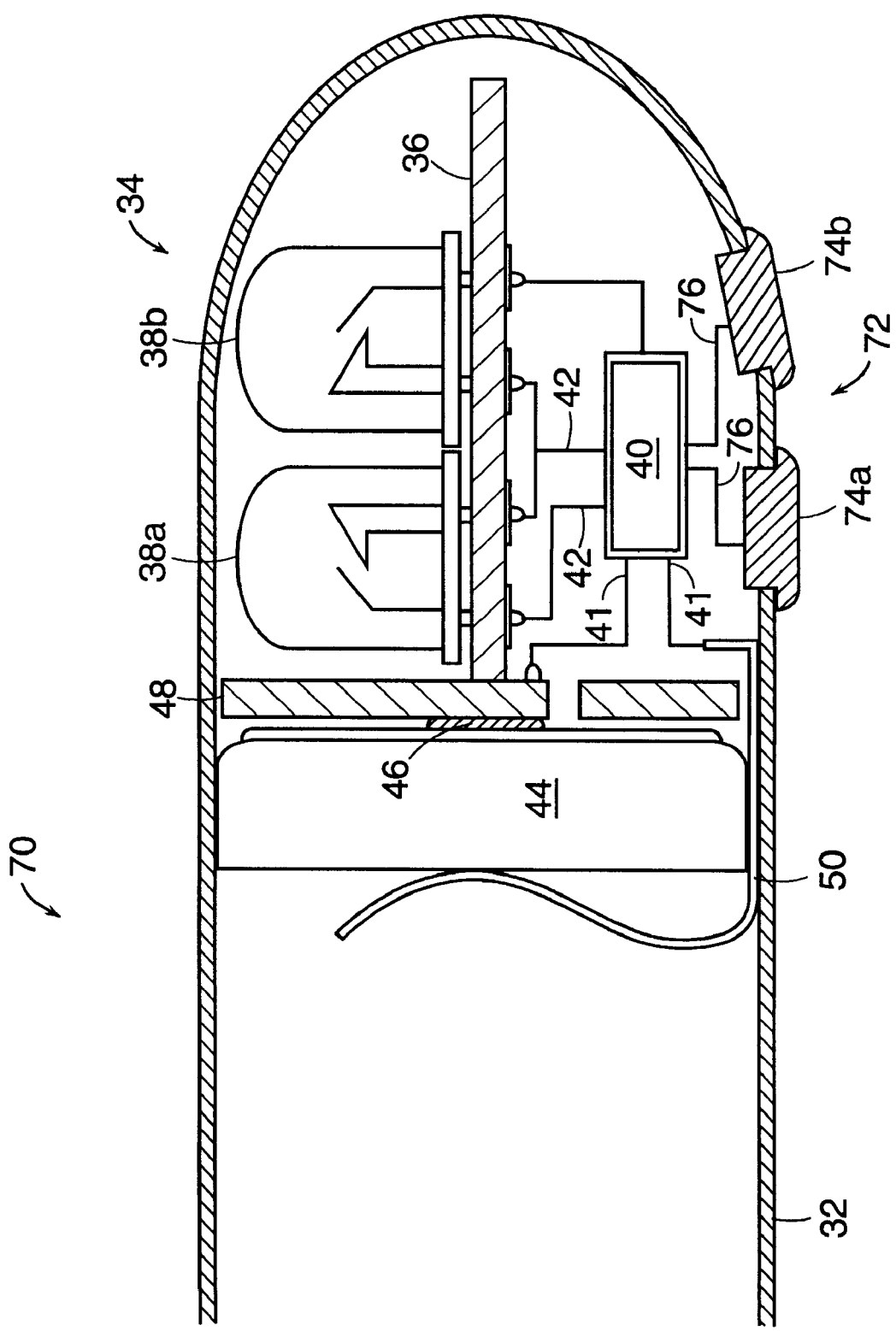
FIG. 3 is a cross-sectional view of an interventional device including electrodes, a display, a signal processor and a power source located at the distal end of the interventional device.

Referring to FIG. 3, an interventional device 70 includes an electrode-based sensing system. The sensing system 72 includes a pair of electrodes 74a, 74b mounted at the distal end of the interventional device 70 for sensing a bodily condition. In operation, the electrodes 74a, 74b a bodily condition and provide corresponding signals to the processor 40 via signal lines 76. In response to the signals received from the sensors 74a, 74b, the processor 40 provides a signal indicative of a bodily condition to one of the LEDs 38a, 38b. One of the LEDs turns ON to display an indication of the sensed bodily condition.

Figure 4:
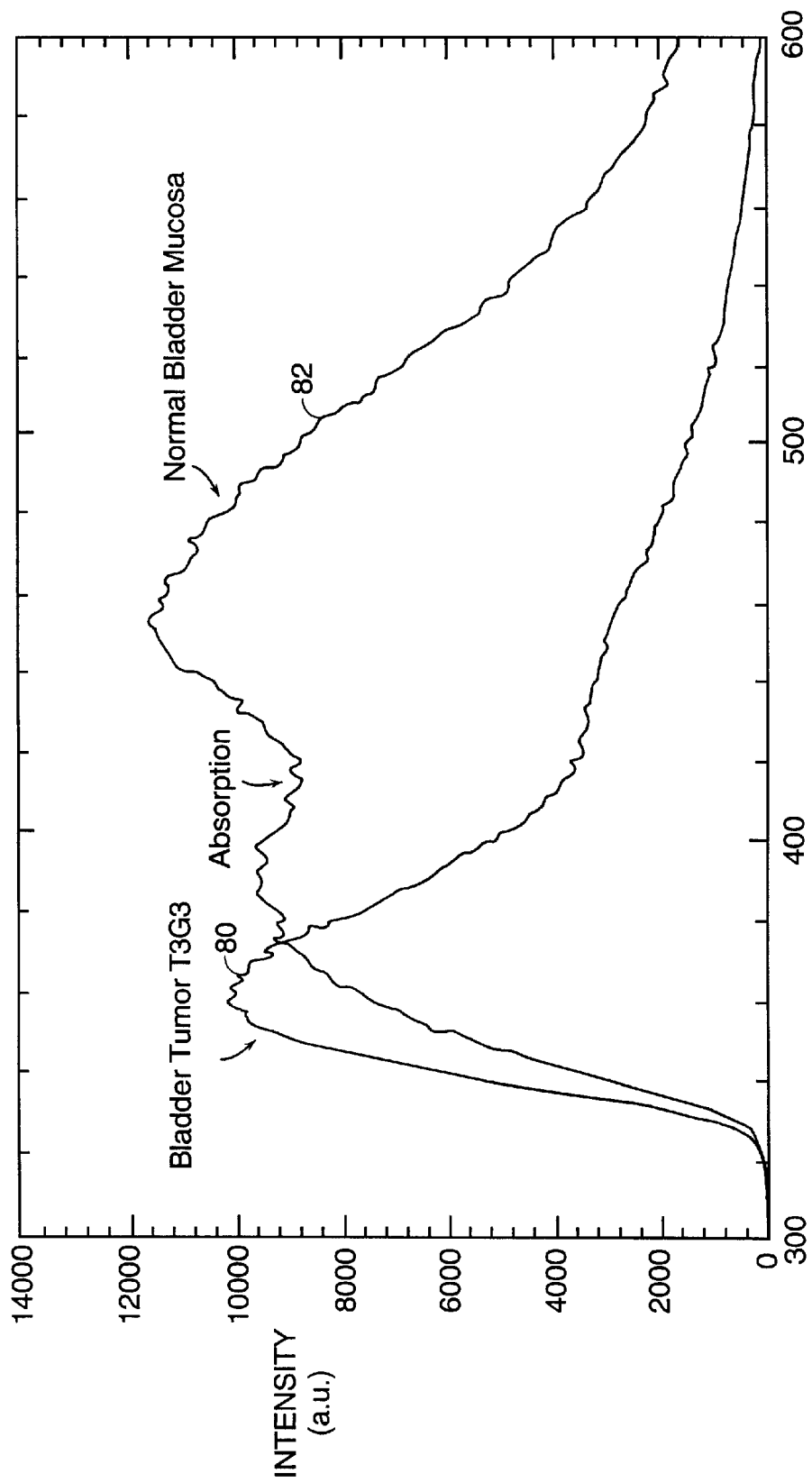
FIGS. 4 is a graph illustrating the fluorescence spectrum for normal and cancerous bladder tissue.

FIG. 4 is a graph illustrating the fluorescence spectrum for normal and cancerous bladder tissue. An excitation wavelength of around 300 nanometers is used to excited suspicious bladder tissue. The resulting tissue fluorescence curves for normal tissue 82 and cancerous tissue 80 is shown. For normal tissue, a peak exists in the 440 to 460 nanometer range. For cancerous tissue, a peak exists in the 370 nanometer range. Both of these spectral responses are in the ultraviolet or blue range of the frequency spectrum and may not be readily visible to the human eye, which has limited sensitivity below 400 nanometers.

Figure 5A:
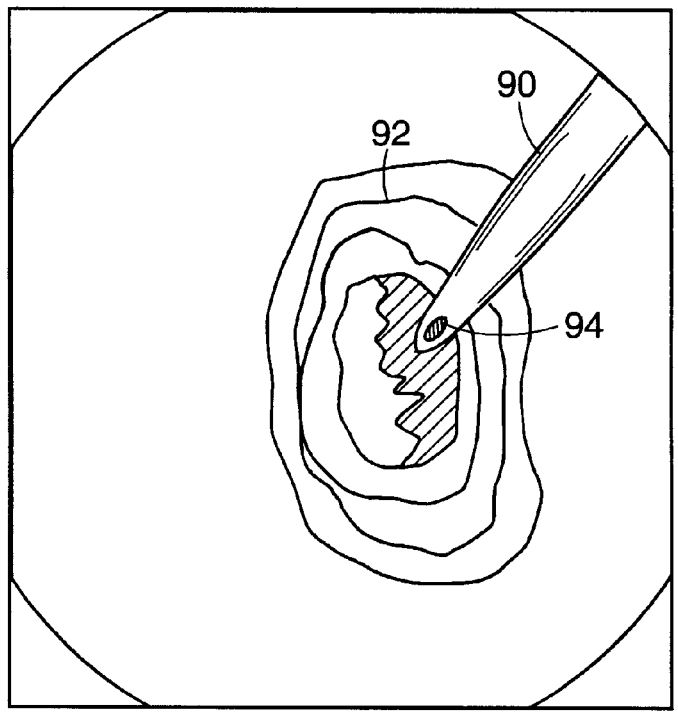
FIGS. 5A and 5B are illustrations of the display located at the distal end of an interventional device for cancerous and normal colon tissue.
Figure 5B:
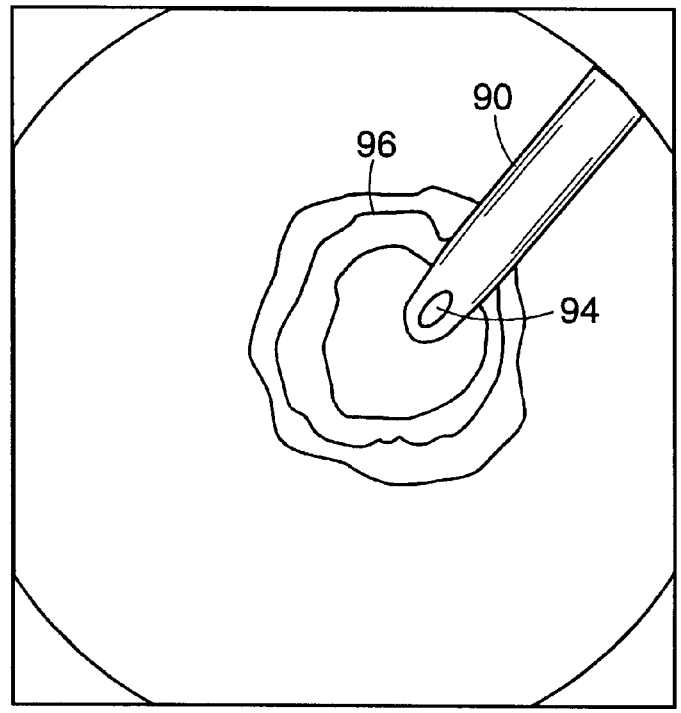

FIGS. 5A and 5B are illustrations of the display located at the distal end of an interventional device for cancerous and normal colon tissue. Referring to FIG. 5A, an interventional device 90 is positioned adjacent tissue 92. The device 90 includes a display 94 having a first color and a second color, both of which can be visible to the human eye. The display can include a pair of LEDs. The sensing system (not shown) senses a bodily condition. In response to the sensed bodily condition, the display 94 generates the first color to indicate cancerous tissue. Referring to FIG. 5B, the interventional device 90 is positioned adjacent tissue 96. The sensing system (not shown) senses a bodily condition. In response to the sensed bodily condition, the display generates the second color to indicate normal tissue.

Equivalents

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An interventional device comprising:
    an elongated member insertible into a body;
    a sensing system disposed in the elongated member at a distal end for sensing a bodily condition, the sensing system including at least one light source and at least one light detector; and
    a display located at the distal end of the elongated member for providing a signal indicative of the bodily condition.

2. The interventional device of claim 1 wherein the display further comprises an indicator which provides a visible signal indicative of a bodily condition.

3. The interventional device of claim 2 wherein the indicator comprises at least one light emitter.

4. The interventional device of claim 3 wherein the at least one light emitter comprise (a) a light emitting diode, (b) a liquid crystal display, or (c) a projection display.

5. The interventional device of claim 2 wherein the indicator comprises at least one optical emitter.

6. The interventional device of claim 2 wherein the indicator comprises at least one chemical indicator.

7. The interventional device of claim 6 wherein the at least one chemical indicator comprises a litmus paper.

8. The interventional device of claim 2 wherein the indicator comprises at least one polymeric emitter.

9. The interventional device of claim 8 wherein at least one of the polymeric emitters comprises at least one organic light emitting diode.

10. The interventional device of claim 1 further comprising
    a power source for providing power to the display.

11. The interventional device of claim 10 wherein the display receives the sensed bodily condition from the sensing system and provides a visible signal indicative of the sensed bodily condition.

12. The interventional device of claim 10 wherein the sensing system comprises at least one sensor.

13. The interventional device of claim 12 wherein the at least one sensor comprises an electrode.

14. The interventional device of claim 1 wherein the at least one light detector is adapted for monitoring light emission from at least one light source.

15. The interventional device of claim 14 further comprising at least one filter disposed adjacent the at least one detector for selectively detecting light emission having a pre-determined wavelength.

16. The interventional device of claim 1 wherein the display provides a visible signal indicative of the bodily condition within a pre-existing field of view.

17. The interventional device of claim 1, wherein;
    the display is coupled to the sensing system for receiving the signal indicative of the bodily condition and providing a visible signal indicative of the bodily condition within a pre-existing field of view.

18. A method for observing a signal indicative of a bodily condition comprising:
    inserting an interventional device including a sensing system and a display located at a distal end thereof into a body;
    contacting tissue in the body with the interventional device;
    illuminating the tissue;
    detecting a spectral emission from the illuminated tissue to sense a bodily condition therefrom;
    generating a signal indicative of the sensed bodily condition; and
    viewing the signal indicative of the sensed bodily condition provided by the display.

19. The method of claim 18 further comprising providing a sensing system disposed in the distal end of the interventional device for sensing the bodily condition.

20. The method of claim 18 further comprising providing a visible signal indicative of the bodily condition within a pre-existing field of view.

21. A method for displaying a signal indicative of a bodily condition comprising:
    inserting an interventional device comprising a sensing system and a display located at a distal end thereof into a body;
    manipulating the interventional device to contact a region in the body;
    illuminating the region;
    detecting a spectral emission from the illuminated region for sensing a bodily condition therefrom;
    generating a signal indicative of the sensed bodily condition; and
    displaying the signal indicative of the sensed bodily condition on the display.

* * * * *